United States Patent [19]

Arkell et al.

[11] 3,957,687

[45] May 18, 1976

[54] HYDROALKYLATION CATALYST AND PROCESS

[75] Inventors: Alfred Arkell, Wappingers Falls; John M. Crone, Jr., Fishkill, both of N.Y.

[73] Assignee: Texaco Inc., New York, N.Y.

[22] Filed: Dec. 4, 1972

[21] Appl. No.: 311,612

[52] U.S. Cl. .............................. 252/455 R; 208/137
[51] Int. Cl.² .................... B01J 29/06; C10G 35/06
[58] Field of Search ................. 252/455 R; 208/137

[56] References Cited
UNITED STATES PATENTS

| | | | |
|---|---|---|---|
| 2,763,623 | 9/1956 | Haensel | 252/455 R |
| 2,773,108 | 12/1956 | Peters | 252/455 R X |
| 2,918,510 | 12/1959 | Carr et al. | 252/455 R X |
| 2,961,414 | 11/1960 | Burton et al. | 252/455 R X |
| 2,967,207 | 1/1961 | Miller et al. | 252/455 R X |
| 2,968,634 | 1/1961 | Nahin | 252/455 R X |
| 3,232,864 | 2/1966 | Pollitzer | 252/455 R X |

Primary Examiner—Paul F. Shaver
Attorney, Agent, or Firm—T. H. Whaley; C. G. Ries; Carl G. Seutter

[57] ABSTRACT

Catalytic activity of a catalyst composition containing a Group VIII metal on an acidic oxide support consisting essentially of a silica alumina cracking catalyst may be increased by the process which comprises
 calcining said catalyst composition at 1350°–1450°F for at least about 2 hours thereby forming a calcined catalyst composition; and
 reducing said calcined catalyst composition at temperature of above about 850°F. for at least about 8 hours thereby forming a catalyst composition characterized by increased activity.

17 Claims, No Drawings

HYDROALKYLATION CATALYST AND PROCESS

BACKGROUND OF THE INVENTION

This invention relates to hydroalkylation. More specifically it relates to a method of increasing the activity of a catalyst which may be used in the hydroalkylation of benzene to form cyclohexylbenzene at high productivity.

As is well known to those skilled in the art, catalysts may be used in a wide variety of processes including hydroalkylation, disproportionation, transalkylation, isomerization, cracking, reforming, hydrodewaxing etc. Typical of such catalysts may be those containing a support on which is deposited an active component.

In the case of hydroalkylation catalysts, they are commonly dual site catalysts providing for centers of hydrogenation activity and for centers of alkylation activity. Typically such catalysts may contain a support such as silica-alumina or zeolite on which is mounted on active metal, typically a Group VIII metal.

Efficient operation requires that the catalyst possess as high a degree of activity as is possible; and to this end various pretreatment processes have been employed. Various techniques may include calcining at temperatures up to 1700°F. for times up to 8 hours followed by reduction at temperatures to 750°F. for times up to 2 hours or to higher temperatures of eg 1000°F. for one hour.

The degree of activation achieved by such techniques has heretofore been less than desired; and it has frequently been found that the improvement is not obtained at a cost which renders the treatment economical.

It is an object of this invention to provide a method of increasing the activity of a catalyst. It is another object of this invention to provide a method of hydroalkylation. Other objects will be apparent to those skilled in the art.

STATEMENT OF THE INVENTION

In accordance with certain of its aspects, the method of this invention for increasing the catalytic activity of a catalyst composition containing a Group VIII metal on an acidic oxide support consisting essentially of a silica-alumina cracking catalyst may comprise calcining said catalyst composition at 1350°F.–1450°F. for at least about 2 hours thereby forming a calcined catalyst composition; and reducing said calcined catalyst composition at temperature of above about 850°F. for at least about 8 hours thereby forming a catalyst composition characterized by increased activity.

DESCRIPTION OF THE INVENTION

The catalyst compositions which may be treated by the process of this invention may typically be dual-site hydroalkylation catalysts which are characterized by the presence of centers of hydrogenation activity and of alkylation activity. These catalyst compositions may include a support which may include as an acidic oxide support, a silica-alumina cracking catalyst typically containing about 10–30% alumina and the balance of 70–90% essentially silica.

Typical of the silica alumina cracking catalysts may be a low alumina catalyst containing eg 13% aluumina and 86.8% silica (such as that sold under the designation F-1-13 by Davidson Chemical Division of Grace) or a high alumina catalyst containing eg 28% alumina and 71.6% silica (such as that sold under the designation F-1-25 by Davison).

The support material, preferably a low alumina, silica-alumina may be impregnated with a Group VIII transition metal component e.g. cobalt, nickel, ruthenium, rhodium, palladium, iridium, and platinum. When the Group VIII metal is Co or Ni, it will preferably be present in amount of 2–30%, typically 4–25%, say 5%. When the Group VIII metal is a noble metal, i.e. a metal having an atomic number greater than 28, it may be present in amount of 0.2–5%, san 1%.

In typical embodiments, the catalyst composition may also include 0–30%, preferably 10–20%, say 19% of a Group VI metal such as Cr, Mo, or W, preferably W.

A typical catalyst composition may be prepared by immersing F-1-13 silica-alumina catalyst in nickel nitrate solution and then drying the catalyst in air at 100°C. to form a green catalyst containing (on a dry basis) 6% nickel on silica-alumina. Optionally such a catalyst may be mixed with eg 4–6, say 5 times its weight of untreated silica alumina.

It is a feature of the method of this invention for increasing the catalytic activity of such a catalyst that it be calcined at 1350°–1450°F., and preferably at about 1400°F. Calcining temperatures below this range (e.g. at 1200°F.) commonly are found to have little or no effect on the productivity of the catalyst. Calcining temperatures above this range (eg at 1500°F.) commonly are found to cause a decrease in the productivity of the catalyst. Calcining of the catalyst is preferably effected for at least about 2 hours and preferably 2–4 hours.

Preferably calcining is carried out in ambient atmosphere; and in typical operation, a stream of air may be passed over the catalyst during calcining.

During the vigorous calcining, the catalyst is dried and the charge compounds (e.g. nickel nitrate) are decomposed to form the corresponding metals, or more commonly the oxides, which interact with the support.

In practice of the process of this invention, the calcined catalyst may be reduced at temperature above about 850°F., preferably 900°–1000°F. say about 900°F. for at least about 8 hours, preferably 8–16 hours, say about 8 hous. While it may be possible to achieve operative catalyst by the use of reducing temperature below 850°F., it is found that maximum productivity is not achieved unless the temperature of reduction is 850°F. or greater. Within the preferred range, it may be possible to gain additional improvement, but this is accomplished under economically less desirable conditions; accordingly reduction may preferably be carried out at about 900°F.

It will be observed in practice of this invention that a catalyst (e.g. 5% nickel on a low alumina, silica-alumina catalyst) which has been calcined for 2 hours, may permit attainment of increased productivity by the process of this invention typically by 17% — while one which has been calcined for 4 hours may improve productivity by typically as much as 100%.

Use of the so pretreated catalyst in a hydroalkylation may be effected by passing 100 parts of charge aromatic hydrocarbon, typically benzene (or a substituted benzene such as toluene, etc.) to a hydroalkylation operation. Hydroalkylation may be carried out at an inlet temperature of 25°–300°C., preferably 100°–200°C., say 130°C. at 100–1500 psig, say 500 psig. The pressure is normally sufficient to maintain the reactants (except for the hydrogen gas) in liquid phase.

Hydroalkylation may be effected in the presence of a hydroalkylation catalyst and a hydroalkylating quantity of hydrogen. Hydrogen may be present in amount of 0.3–3 parts, say 1.8 parts. The hydrogen need not be pure; but preferably hydrogen of 80–95% purity may be used. The hydrogen should preferably be free of any impurities which may poison the catalyst. Hydrogen recovered from a reforming operation may be suitable.

Preferably hydroalkylation may be effected at an LHSV of 0.5–15, typically 2–6, say 2.

In preferred operation, the charge to hydroalkylation may thus include 100 parts of benzene and 0.3–3 parts of hydrogen.

Product effluent from hydroalkylation in practice of the process of this invention may typically include the following:

TABLE

| Component | Parts Broad | Typical |
|---|---|---|
| Benzene | 65–81 | 67.5 |
| Cyclohexylbenzene | 11–23 | 22.8 |
| Dicyclohexylbenzene* | 2–6 | 5.9 |
| Methylcyclopentane | 0.1–0.3 | 0.2 |
| Cyclohexane | 3–10 | 3.6 |

*and heavier

It is a particular feature of the method of this invention that it may be possible to obtain productities of 120 grams of cyclohexylbenzene per hour per 100 cc of catalyst — or more. Typically it may be found that productivities of 140 to 200 may be achieved. It is unexpected for example to be able to take a catalyst which has been calcined (in a control example) at 1400°F. for 2 hours for example and to increase its productivity (in an experiment) from an initial value of 140 to an improved value of 160. It is even more unexpected for example to be able to take the same catalyst which had been calcined (in another control example) at 1400°F for 4 hours and to find that use of the novel process of this invention permits attainment of a doubled productivity — increase from 100 to a value of 200.

DESCRIPTION OF PREFERRED EMBODIMENT

Practice of the process of this invention may be apparent to those skilled in the art from the following wherein, as elsewhere in this description unless otherwise specified, all parts are parts by weight.

EXAMPLES I–IV

In this series of Examples, the catalyst may be prepared from Davison F-1-13 Low Alumina silica-alumina which contains 13% alumina and 86.8% silica and is characterized by a 59 micron average particle size. 100 Parts of this charge are immersed in an aqueous solution of nickel nitrate for 8 hours; and the charge is drained and dried at 100°C to yield a product catalyst containing 5% nickel on F1-13 silica-alumina.

In control example I, this catalyst is calcined at 1400°F. for 2 hours in air and then reduced in flowing hydrogen at 800°F. for 0.5 hours.

In experimental Example II, the catalyst is calcined at 1400°F. for 2 hours and then reduced in flowing hydrogen at 900°F. for 16 hours.

In control Example III, the catalyst is calcined at 1400°F. for 4 hours and then reduced in flowing hydrogen at 800°F. for 0.5 hours.

In experimental Example IV, the catalyst is calcined at 1400°F. for 4 hours and then reduced in flowing hydrogen at 900°F for 15 hours.

Each of the catalysts of Examples I–IV was used as a hydroalkylation catalyst under comparable conditions. In a typical run, 39 parts of benzene and 2.25 parts of catalyst are added to a pressure vessel-reactor which is purged, pressure-tested, and heated to 370°–380°F. The vessel is then pressured with hydrogen to a fixed pressure of 500 psig. A ballast tank is adjusted to 1100 psig. A run is continued until the total hydrogen uptake, as measured on the ballast tank gauge, is 150 psig. The reactor contents are then analyzed. The following Table indicates the weight percent yield of each of the products and the productivity in terms of grams of cyclohexylbenzene per hour per 100 cc of catalyst.

TABLE

| Item | Example I* | II | III* | IV |
|---|---|---|---|---|
| Product | | | | |
| Methylcyclopentane | 0.2 | 0.2 | 0.1 | 0.2 |
| Cyclohexane | 4.2 | 6.0 | 3.8 | 3.6 |
| Cyclohexylbenzene | 19.5 | 19.1 | 18.9 | 22.8 |
| Dicyclohexylbenzene | 5.5 | 4.6 | 4.6 | 5.9 |
| Reaction Time (Hr.) Time required for 150 psig H$_2$ Uptake | 1.42 | 1.14 | 1.67 | 1.15 |
| Productivity | 143 | 163 | 99 | 191 |

*Control

From the above table, it will be apparent from a comparison of Examples I and II, that use of a catalyst which has been treated by the process of this invention (Example II) permits attainment of productivity which is increased by a factor of (163/143) 1.14 i.e. an increase of 14% over the control of Example I. In the second pair of examples, it is apparent that use of a catalyst which has been treated by the process of this invention (Example IV) permits attainment of productivity which is increased by a factor of (191/99) 1.93 i.e. almost double that of the control of Example III.

Productivity is defined as the amount of desired product obtained per unit volume of catalyst. In the hydroalkylation of Examples I–IV, productivity is calculated as grams of desired cyclohexylbenzene per hour per 100 cc of catalyst.

Although this invention has been illustrated by reference to specific embodiments, it will be apparent to those skilled in the art that various changes and modifications may be made which clearly fall within the scope of this invention.

We claim:

1. The method of increasing the catalytic activity of a catalyst composition containing a Group VIII metal on an acidic oxide support consisting essentially of a silica-alumina cracking catalyst which comprises calcining said catalyst composition at 1350°–1450°F for at least about 2 hours thereby forming a calcined catalyst composition; and reducing said calcined catalyst composition at temperature of above about 850°F and less than about 1000°F for at least about 8 hours thereby forming a catalyst composition characterized by increased activity.

2. The method of increasing the catalytic activity of a catalyst composition as claimed in claim 1 wherein said Group VIII metal is cobalt or nickel.

3. The method of increasing the catalytic activity of a catalyst composition as claimed in claim 1 wherein said silica-alumina catalyst contains 10–30% alumina and the balance is essentially silica.

4. The method of increasing the catalytic activity of a catalyst composition as claimed in claim 1 wherein said silica-alumina catalyst is a low-alumina silica-alumina.

5. The method of increasing the catalytic activity of a catalyst composition as claimed in claim 1 wherein said silica-alumina catalyst contains about 13% alumina and about 87% silica.

6. The method of increasing the catalytic activity of a catalyst composition as claimed in claim 1 wherein said silica-alumina catalyst is a high-alumina silica-alumina.

7. The method of increasing the catalytic activity of a catalyst composition as claimed in claim 1 wherein said silica-alumina catalyst contains about 28% alumina and about 72% silica.

8. The method of increasing the catalytic activity of a catalyst composition as claimed in claim 1 wherein said calcining is carried out at about 1400°F.

9. The method of increasing the catalytic activity of a catalyst composition as claimed in claim 1 wherein said calcining is carried out for about 2–4 hours.

10. The method of increasing the catalytic activity of a catalyst composition as claimed in claim 1 wherein said reducing is carried out at temperature of above about 900°F. and less than about 1000°F.

11. The method of increasing the catalytic activity of a catalyst composition as claimed in claim 1 wherein said reducing is carried out at about 900°F.

12. The method of increasing the catalytic activity of a catalyst composition as claimed in claim 1 wherein said reducing is carried out for 8–16 hours.

13. The method of increasing the catalytic activity of a catalyst composition containing nickel or cobalt on a low alumina consisting essentially of 13% alumina and 87% silica which comprises
    calcining said catalyst composition at 1350°–1450°F for about 2–4 hours thereby forming a calcined catalyst composition; and
    reducing said calcined catalyst composition at temperature above about 900°F and less than about 1000°F for 8–16 hours.

14. An activated catalyst composition containing a Group VIII metal on an acidic oxide support consisting essentially of a silica-alumina cracking catalyst prepared by the process which comprises
    calcining said catalyst composition at 1350°–1450°F. for at least about 2 hours thereby forming a calcined catalyst composition; and
    reducing said calcined catalyst composition at temperature of above about 850°F. for at least about 8 hours thereby forming a catalyst composition characterized by increased activity.

15. An activated catalyst composition containing a Group VIII metal on an acidic oxide support consisting essentially of a silica-alumina cracking catalyst as claimed in claim 14 prepared by the process which comprises
    calcining said catalyst composition at 1350°–1450°F for about 2–4 hours thereby forming a calcined catalyst composition; and
    reducing said calcined catalyst composition at temperature above 900°F and less than about 1000°F for 8–16 hours.

16. The process for hydroalkylating a charge benzene with a hydroalkylating quantity of hydroalkylating quantity of hydrogen which comprises contacting said charge benzene with hydrogen at hydroalkylating conditions in the presence of a catalyst composition containing a Group VIII metal on an acidic oxide support consisting essentially of a silica-alumina cracking catalyst, said catalyst composition having been activated by the process which comprises
    calcining said catalyst composition at 1350°–1450°F. for at least about 2 hours thereby forming a calcined catalyst composition; and
    reducing said calcined catalyst composition at temperature of above about 850°F. for at least about 8 hours thereby forming a catalyst composition characterized by increased activity.

17. The method of increasing the catalytic activity of a catalyst composition containing a Group VIII metal on an acidic oxide support consisting essentially of a silica-alumina cracking catalyst which comprises
    calcining said catalyst composition at about 1400°F for at least about 2 hours thereby forming a calcined catalyst composition; and
    reducing said calcined catalyst composition at temperature of above about 850°F and less then about 1000°F for at least about 8 hours thereby forming a catalyst composition characterized by increased activity.

* * * * *

UNITED STATES PATENT AND TRADEMARK OFFICE
CERTIFICATE OF CORRECTION

PATENT NO. : 3,957,687

DATED : May 18, 1976

INVENTOR(S) : A. Arkell and J. Crone, Jr.

It is certified that error appears in the above-identified patent and that said Letters Patent are hereby corrected as shown below:

col. 1 line 68      correct "Davidson" to --Davison-- col. 2 line 13      correct "san" to --say-- col. 3 line 65      correct "F1-13" to --F-1-13--

Signed and Sealed this

Thirty-first Day of October 1978

[SEAL]

Attest:

RUTH C. MASON
Attesting Officer

DONALD W. BANNER
Commissioner of Patents and Trademarks